US007846726B2

(12) United States Patent
Li et al.

(10) Patent No.: US 7,846,726 B2
(45) Date of Patent: Dec. 7, 2010

(54) HUMAN FETAL BLADDER-DERIVED EPITHELIAL CELLS

(75) Inventors: Ronghao Li, Millbrae, CA (US); Zhuangyu Pan, Millbrae, CA (US)

(73) Assignee: Raven biotechnologies, inc., South San Francisco, CA (US)

( * ) Notice: Subject to any disclaimer, the term of this patent is extended or adjusted under 35 U.S.C. 154(b) by 456 days.

(21) Appl. No.: 10/366,032

(22) Filed: Feb. 12, 2003

(65) Prior Publication Data

US 2003/0211090 A1 Nov. 13, 2003

Related U.S. Application Data

(60) Provisional application No. 60/357,035, filed on Feb. 12, 2002.

(51) Int. Cl.
*C12N 5/00* (2006.01)
*C12N 5/02* (2006.01)
*C12N 5/08* (2006.01)

(52) U.S. Cl. .............. 435/378; 435/325; 435/366; 435/371; 435/384; 435/389

(58) Field of Classification Search .......... 435/325, 435/366, 371, 378, 384, 389
See application file for complete search history.

(56) References Cited

U.S. PATENT DOCUMENTS

| 6,416,999 B1 * | 7/2002 | Li et al. ............ 435/366 |
| 6,617,161 B2 * | 9/2003 | Luyten et al. ........ 435/375 |
| 6,759,039 B2 * | 7/2004 | Tsang et al. ........ 424/93.7 |

FOREIGN PATENT DOCUMENTS

| EP | 1 000 541 A1 * | 5/2000 |
| WO | WO 96/40866 * | 12/1996 |
| WO | WO 98/59035 * | 12/1998 |
| WO | WO 00/37503 | 6/2000 |
| WO | WO0177298 A2 | 10/2001 |
| WO | WO 02/102997 | 12/2002 |
| WO | WO-03/068938 A2 | 8/2003 |
| WO | WO-03/068938 A3 | 8/2003 |
| WO | WO-01/49827 A1 | 7/2007 |

OTHER PUBLICATIONS

Stojkovic et al., 2004, Reproduction, vol. 128, p. 259-267.*
Bodnar et al., 2004, Stem Cells and Development, vol. 13, p. 243-253.*
Bhatia, M., 2003, Cloning and Stem Cells, vol. 5, No. 1, p. 89-97.*
ATCC Catalogue of Cell Lines & Hybridomas, 7th Edition, 1992, ATCC HTB 160, FHs 738B1, p. 271.*
Elkin et al., 1998, Carcinogenesis, vol. 19, No. 12, pp. 2095-2099.*
Hammond et al., 1984, PNAS, vol. 81, pp. 5435-5439.*
Von Koskull et al., 1984, Human Genetics, vol. 65, p. 262-267.*
Cliento et al., 1994, The Journal of Urology, vol. 152, p. 665-670.*
Ausubel, F.M. et al. eds. (1987). *Current Protocols in Molecular Biology* John Wiley & Sons, Inc. pp. iii-xii (Table of Contents Only.).

Ayres, P.H. et al. (1984). "A Rapid Method For Preparation of Urinary Bladder Epithelium For Flow Cytometric Analysis," *The Journal of Urology* 131:1202-1205.
Barnes, D. and Sato, G. (1980). "Methods For Growth of Cultured Cells in Serum-Free Medium," *Anal. Biochem.* 102:255-270.
Baskin, L.S. et al. (1996). "Mesenchymal-Epithelial Interactions in the Bladder," *World Journal of Urology* 14:301-309.
Baskin, L.S. et al. (1999). "Epithelial-Mesenchymal Interactions in the Bladder—Implications for Bladder Augmentation" Chapter 5 *In Advances in Experimental Medicine and Biology* Plenum Press: New York, NY vol. 462, pp. 49-61.
Buck, D.W. et al. (1982). "Monoclonal Antibodies Specific For Cell Culture Mycoplasmas," *In Vitro* 18(4):377-381.
Christensen, B. et al. (1984). "A Classification of Human Urothelial Cells Propagated in Vitro," *Anticancer Res.* 4:319-337.
Cooper, M.J. et al. (1996). "Developmentally Imprinted Genes as Markers for Bladder Tumor Progression," *The Journal of Urology* 155:2120-2127.
Cunha, G.R. et al. (1983). "Heterospecific Induction of Prostatic Development in Tissue Recombinants Prepared With Mouse, Rat, Rabbit and Human Tissues," *Differentiation* 24:174-180.
Elkin, M. et al. (1995). "The Expression of the Imprinted H19 and IGF-2 Genes in Human Bladder Carcinoma," *FEBS Lett.* 374:57-61.
Freshney, R.I. ed. (1987). *Culture of Animal Cells: A Manual of Basic Techniques* Second Edition, Alan R. Liss, Inc.: New York, NY. pp. vii-xiv (Table of Contents Only.).
Gillenwater, J. et al. (2002). *Adult and Pediatric Urology* Lippincott Williams & Wilkins: Philadelphia, PA. vol. 1, five pages (Table of Contents Only.).
Ham, R.G. and McKeehan, W.L. (1979). "Media and Growth Requirements," Chapter 5 *In Methods in Enzymology* Academic Press, Inc. vol. 58, pp. 44-93.
Harlow, E. and Lane, D., eds. (1988). *Antibodies, A Laboratory Manual* Cold Spring Harbor Laboratory Press: Cold Spring Harbor, New York. (Table of Contents Only.).
Hu, P. et al. (2000). "Ablation of Uroplakin III Gene Results in Small Urothelial Plaques, Urothelial leakage, and Vesicoureteral Reflux," *J. Cell Biol.* 151(5):961-972.
Jen, P.Y.P. et al. (1995). "Immunohistochemical Localization of Neuromarkers and Neuropeptides in Human Fetal and Neonatal Urinary Bladder," *British Journal of Urology* 75:230-235.
Keay, S. et al. (1996). "Decreased H-Thymidine Incorporation by Human Bladder Epithelial Cells Following Exposure To Urine From Interstitial Cystitis Patients," *The Journal of Urology* 156:2073-2078.
Kohler, G. and Milstein, C. (1975). "Continuous Cultures of Fused Cells Secreting Antibody of Predefined Specificity," *Nature* 256:495-497.

(Continued)

*Primary Examiner*—Shin-Lin Chen
(74) *Attorney, Agent, or Firm*—Jeffrey I. Auerbach; Edell, Shapiro & Finnan, LLC

(57) ABSTRACT

This invention discloses a substantially pure population of human urinary bladder-derived epithelial cells and methods of isolating and culturing the urinary bladder-derived epithelial cells. In addition, several uses of human urinary bladder-derived epithelial cells and cells differentiating therefrom are disclosed herein.

5 Claims, 3 Drawing Sheets

OTHER PUBLICATIONS

Lipschutz, J.H. et al. (1996). "Urothelial Transformation Into Functional Glandular Tissue In Situ, By Instructive Medesenchymal Induction," *Kidney International* 49:59-66.

Liu, W. et al. (2000). "Diffusable Growth Factors Induce Bladder Smooth Muscle Differentiation," *In Vitro Cell. Dev. Biol.* 36(7):476-484.

Mather, J.P. and Roberts, P.E. (1998). *Introduction to Cell and Tissue Culture* Plenum Press: New York, NY. pp. xi-xv. (Table of Contents Only.).

McPherson, M.J. et al eds. (1995). *PCR 2: A Practical Approach* IRL Press pp. ix-xvii (Table of Contents Only.).

Moll, R. et al. (1993). "Uroplakin III, A Specific Membrane Protein of Urothelial Umbrella Cells, As Histological Markers for Metastatic Transitional Cell Carcinomas," *Verh. Deutsc. Ges. Pathol.* 77:260-265. (English Abstract.).

Moll, R. et al. (1995). "Uroplakins, Specific Membrane Proteins of Urothelial Umbrella Cells, as Histological Markers of Metastatic Transitional Cell Carcinomas," *Am J. Pathol.* 147(5):1383-1397.

Nathrath, W.B.J. et al. (1979). "Species Cross-Reacting Epithelial and Urothelial Specific Antigens in Human Fetal, Adult, and Neoplastic Bladder Epithelium," *Journal of the National Cancer Institute* 63(6):1323-1330.

Owens, R.B. et al. (1976). "Brief Communication: Epithelial Cell Cultures From Normal and Cancerous Human Tissues," *Journal of the National Cancer Institute* 56(4):843-849.

Sambrook, J. et al. (1989). *Molecular Cloning: A Laboratory Manual*, Second Edition. Cold Spring Harbor Laboratory Press: Cold Spring Harbor, NY. pp. xi-xxxviii (Table of Contents Only.).

Smith, L.T. (1992). "Separation of Noncutaneous Epithelia In A Fetus Diagnosed in Utero with Junctional Epidermolysis Bullosa," *Pediatric Research* 31(6):561-566.

Summerhayes, I.C. (1988). "Transplantation of Immortalized Bladder Epithelial Cell Lines in Denuded Mouse Bladder," *The Journal of Urology* 139(2):405-409.

Truschel, S.T. et al. (1999). "Primary Uroepithelial Cultures: A Model System To Analyze Umbrella Cell Barrier Function," *The Journal of Biological Chemistry* 274(21):15020-15029.

Von Koskull, H. et al. (1984). "Identification of Cells from Fetal Bladder Epithelium in Human Amniotic Fluid," *Human Genetics* 65:262-267.

Yu, J. et al. (1992). "Identification of an 85-100 kDa Glycoprotein as a Cell Surface Marker for an Advanced Stage of Urothelial Differentiation: Association with the Inter-Plaque ('Hinge') Area," *Epith. Cell Biol.* 1:4-12.

International Search Report mailed Jun. 3, 2004, for PCT Application No. PCT/US03/04547, filed Feb. 12, 2003, three pages.

Newman, J. et al. (1989). "The Fine Structure of the Human Fetal Urinary Bladder. Development and Maturation. A Light, Transmission and Scanning Electron Microscopic Study," *J. Anat.* 166:135-150.

Aboseif, S. et al. (Oct. 1999). "Mesenchymal Reprogramming of Adult Human Epithelial Differentiation," *Differentiation* 65(2):113-118.

Kirk, D. et al. (Mar. 1985). "Selective Growth of Normal Adult Human Urothelial Cells in Serum-Free Medium," *In Vitro Cellular and Developmental Biology* 21(3, Part I):165-171.

Reznikoff, C.A. et al. (Apr. 1983). "Growth and Characterization of Normal Human Urothelium In vitro," *In Vitro* 19(4):326-343.

Scriven, S.D. et al. (Sep. 1997). "Reconstitution of Human Urothelium from Monolayer Cultures," *The Journal of Urology* 158(3, Part 2 of 2):1147-1152.

Southgate, J. et al. (Oct. 1994). "Normal Human Urothelial Cells In vitro: Proliferation and Induction of Stratification," *Laboratory Investigation* 71(4):583-593.

Suematsu, N. et al. (1991). "Analysis of Epithelial Protein Profiles of Prostatic Glands Induced Heterotypically in the Bladder Epithelium of the Rat," *Development Growth & Differentiation* 33(4):379-389.

Allen, et al., "Rapid Degradation of Extracellular Matrix Proteins by Normal Human Uroepithelial Cells", Cancer Research, vol. 50 pp. 1897-1904, Mar. 15, 1990.

Ayesh, et al., "Possible Physiological Rose of H19 RNA", Molecular Carcinogenesis, vol. 35, pp. 63-74, 2002.

Baker, et al., "Embryonic Development of the Ureter and Bladder: Acquisition of Smooth Muscle", The Journal of Urology, vol. 160, pp. 545-550, Aug. 1998.

Banet, et al., "Characterization of Human and Mouse H19 Regulatory Sequences", Molecular Biology Reports, vol. 27, pp. 157-165, Sep. 6, 2000.

Berteaux, et al., "Hormonal Regulation of H19 Gene Expression in Prostate Epithelial Cells", Journal of Endocrinology, vol. 183, pp. 69-78, 2004.

Fowden, et al., "Imprinted Genes, Placental Development and Fetal Growth", Hormone Research, vol. 65, pp. 50-58, 2006.

Freeman, et al., "Heparin-binding EGF-Like Growth Factor is an Autocrine Growth Factor for Human Urothelial Cells and is Synthesized by Epithelial and Smooth Muscle Cells in the Human Bladder", The American Society for Clinical Investigation, Inc., vol. 99, No. 5, pp. 1028-1036, Mar. 1997.

Goshen, et al., "The Expression of the H-19 and IGF-2 Genes During Human Embryogenesis and Placental Development", Molecular Reproduction and Development, vol. 34, pp. 374-379, 1993.

Matouk, et al., "Oncofetal Splice-Pattern of the Human H19 Gene", Biochemical and Biophysical Research Communications, vol. 318, pp. 916-919, 2004.

Moll, et al., "Cytokeratins in Normal and Malignant Transitional Epithelium", American Journal of Pathology, vol. 132, No. 1, pp. 123-144, Jul. 1988.

Oottamasathien, et al., "Bladder tissue Formation From Cultured Bladder Urothelium", Developmental Dynamics, vol. 235, pp. 2795-2801, May 26, 2006.

Virtanen, et al., "Cultured Human Amniotic Fluid Cells Characterized with Antibodies Against Intermediate Filaments in Indirect Immunofluorescence Microscopy", The Americana Society for Clinical Investigation, Inc., vol. 68, pp. 1348-1355, Nov. 1981.

Lustig, et al., "Expression of the Imprinted Gene H19 in the Human Fetus", Molecular Reproduction and Development, vol. 38, pp. 239-246, 1994.

* cited by examiner

HUMAN FETAL BLADDER-DERIVED EPITHELIAL CELLS

REFERENCE TO RELATED APPLICATIONS

The application claims priority under 35 U.S.C. §119(e) to U.S. Provisional Patent Application Ser. No. 60/357,035, filed Feb. 12, 2002, the entirety of which is incorporated herein by reference.

TECHNICAL FIELD

The invention relates to the field of developmental biology and cell biology, and more particularly to purified fetal human bladder-derived epithelial cells and fetal human bladder epithelium cell lines.

BACKGROUND ART

The human urinary bladder is essentially a two-layered organ, consisting of a muscular outer wall and a highly specialized epithelium lining the lumen. Differentiated urinary bladder epithelium is characterized by the presence of urothelial plaques on the lumenal surface of urinary bladder superficial or umbrella cells. These plaques are characterized by a highly unusual membrane structure, i.e., the asymmetric unit membrane (AUM), with a lumenal leaflet twice as thick as the cytoplasmic leaflet. The thickening of the lumenal leaflet is due to the presence of particles exhibiting a semi-crystalline organization and made up principally of four transmembrane proteins: uroplakin (UP) Ia (27 kDa); UP Ib (28 kDa); UP II (15 kDa) and UP III (47 kDa). UP III is believed to play a role in the formation of the urothelial glycocalyx and may interact, via its cytoplasmic portion, with the cytoskeleton. Hu et al., 2000. *J. Cell Biol.* 151(5):961-72.

The developmental origin of the urinary bladder is found in endodermal tissue. The bladder arises from the cloaca, a common chamber from which both the bladder and the lower alimentary canal are derived. As development proceeds, the cloaca is divided into the hind gut and the urogenital sinus. The muscular wall of the bladder is induced from the adjacent mesenchyme by signals from bladder epithelium, although the identity of the signal(s) is unknown.

Amongst men in the U.S., bladder cancer accounts for approximately 2% of all malignant tumors and approximately 7% of all urinary tract malignancies, although women experience approximately one-third the incidence of men. Additionally, race plays a factor, with African-American men experiencing nearly twice the age-adjusted incidence of non-Hispanic white males. The American Cancer Society estimates there will be more than 50,000 new bladder cancer cases in the next year, with an estimated 9,500 deaths. For superficial, low-grade disease, chemotherapy is applied intravesically (directly into the bladder) to concentrate the drug at the tumor site and eliminate any residual tumor mass after resection. Systemic chemotherapy and/or radiation are used on high grade disease, commonly in conjunction with radical cystectomy. However, because about 50% of patients with high-stage, high-grade tumors eventually relapse following cystectomy, surgery is seldom performed to palliate symptoms in these patients.

In addition to race and sex factors, chemical exposures are established risk factors for bladder cancer. Chief amongst chemical exposure risk factors are smoking, but occupational exposures, particularly to arylamines, are also significant risk factors.

A number of investigators have described the use of uroplakin antibodies for analysis of the differentiation state of urothelial cells or for diagnosis of metastatic bladder carcinoma. Yu et al., 1992. *Epith. Cell Biol.* 1:4-b 12; Moll et al. 1993 *Verh. Deutsc. Ges. Path.* 77 and Moll et al. 1995. *Am. J. Pathol.* 147:1383-1397.

In vitro investigations of urothelial cells typically utilize cell lines derived from bladder tumors or primary urothelial cells, although a limited number of normal urothelial tissue-derived cell lines have been reported (Christensen et al., 1984, *Anticancer Res.* 4:319-38). International Patent Application WO 02/102997 discloses homozygous stem cells derived from non-fertilized post-meiosis I diploid germ cells which can purportedly be differentiated into a variety of cell types. See also, Keay et al., 1996, *J. Urol.* 156(6):2073-8; and Owens et al., 1976, *J. Natl. Cancer Inst.* 56(4):843-9.

DISCLOSURE OF THE INVENTION

In one aspect, the invention relates to a population of substantially pure human fetal urinary bladder-derived epithelial cells that have a capability to differentiate into urinary bladder epithelium and/or prostatic epithelium. Thus, reference to a capability to differentiate into urinary bladder epithelium or prostatic epithelium indicates a capacity to differentiate into either of the cell types. The cells may be cultured in serum-free nutrient medium, and may have cell surfaces that are substantially free of serum biomolecules. The human fetal urinary bladder-derived epithelial cells of the invention express the H19 marker gene.

In another aspect, the invention provides a method of isolating a substantially pure population of urinary bladder-derived epithelial cells, comprising: (a) maintaining suitable culture conditions sufficient to allow human fetal urinary bladder-derived epithelial cells to form monolayer colonies; wherein the human fetal urinary bladder-derived epithelial cells have been maintained in suitable culture conditions sufficient to allow migration of the urinary bladder-derived epithelial cells from a microdissected source of urinary bladder-derived epithelial cells into a serum-free nutrient media to form the monolayer colonies; wherein the source of urinary bladder-derived epithelial cells have been cultured in the serum-free media under culture conditions sufficient to sustain the urinary bladder-derived epithelial cells, wherein the serum-free media contains nutrients comprising insulin, transferrin, α-tocopherol, and aprotinin; and (b) subculturing said monolayer colonies to obtain a substantially pure population of urinary bladder-derived epithelial cells. In some embodiments, the serum-free nutrient medium further comprises progesterone, keratinocyte growth factor (KGF) and heregulin (HRG).

In another aspect, the invention provides a method for producing a population of substantially pure human fetal urinary bladder-derived epithelial cells by microdissecting a source of human fetal urinary bladder-derived epithelial cells; placing the source of urinary bladder-derived epithelial cells in serum-free nutrient media under culture conditions sufficient to sustain said urinary bladder-derived epithelial cells, wherein the serum-free media contains nutrients comprising insulin, transferrin, α-tocopherol, and aprotinin; maintaining suitable culture conditions sufficient to allow migration of urinary bladder-derived epithelial cells from the source of urinary bladder-derived epithelial cells into the serum-free nutrient media; maintaining suitable culture conditions sufficient to allow urinary bladder-derived epithelial cells to form monolayer colonies; and subculturing said monolayer colonies to obtain a substantially pure population of urinary bladder-derived epithelial cells. The medium used in the method may further comprise progesterone, keratinocyte growth factor (KGF) and heregulin (HRG). Accordingly, the human fetal urinary-bladder derived epithelial cells of the invention are not derived from germ cells.

In another aspect, the invention provides a substantially pure population of human fetal urinary bladder-derived epithelial cells produced by the process comprising: (a) maintaining suitable culture conditions sufficient to allow human fetal urinary bladder-derived epithelial cells to form monolayer colonies; wherein the human fetal urinary bladder-derived epithelial cells have been maintained in suitable culture conditions sufficient to allow migration of the urinary bladder-derived epithelial cells from a microdissected source of urinary bladder-derived epithelial cells into a serum-free nutrient media to form the monolayer colonies; wherein the source of urinary bladder-derived epithelial cells have been cultured in the serum-free media under culture conditions sufficient to sustain the urinary bladder-derived epithelial cells, wherein the serum-free media contains nutrients comprising insulin, transferrin, $\alpha$-tocopherol, and aprotinin; and (b) subculturing said monolayer colonies to obtain a substantially pure population of urinary bladder-derived epithelial cells. In some embodiments, the serum-free nutrient medium used in said process further comprises progesterone, keratinocyte growth factor (KGF) and heregulin (HRG).

In a further aspect, the invention provides a population of substantially pure human fetal urinary bladder-derived epithelial cells produced by the process of microdissecting a source of human fetal urinary bladder-derived epithelial cells; placing the source of urinary bladder-derived epithelial cells in serum-free nutrient media under culture conditions sufficient to sustain said urinary bladder-derived epithelial cells, wherein the serum-free media contains nutrients comprising insulin, transferrin, $\alpha$-tocopherol, and aprotinin; maintaining suitable culture conditions sufficient to allow migration of urinary bladder-derived epithelial cells from the source of urinary bladder-derived epithelial cells into the serum-free nutrient media; maintaining suitable culture conditions sufficient to allow urinary bladder-derived epithelial cells to form monolayer colonies; and subculturing said monolayer colonies to obtain a substantially pure population of urinary bladder-derived epithelial cells. The medium used in the method may further comprise progesterone, keratinocyte growth factor (KGF) and heregulin (HRG).

In still another aspect, the invention relates to methods of maintaining a population of substantially pure human fetal urinary bladder-derived epithelial cells which have the capacity to differentiate into bladder or prostate epithelium and maintaining or culturing these human fetal urinary bladder-derived epithelial cells such that the cells retain their capacity to differentiate while avoiding senescence.

In still another aspect, the invention relates to methods of providing a source of immunogen to a heterologous recipient and the uses of a substantially pure population of human fetal urinary bladder-derived epithelial cells as an immunogen. In some embodiments, the invention provides a method of providing a source of an immunogen to a heterologous recipient, comprising administering to said recipient a plurality of the human fetal urinary bladder-derived epithelial cells of the invention in an amount effective to induce an immune response in said recipient.

In still another aspect, the invention relates to methods of eliciting an immune response in a heterologous recipient, comprising administering to said recipient a plurality of the human fetal urinary bladder-derived epithelial cells of the invention in an amount effective to induce an immune response in said recipient.

In still another aspect, the invention relates to methods of generating a population of human bladder epithelial cells differentiated from human fetal urinary bladder-derived epithelial cells, comprising administering the human fetal urinary bladder-derived epithelial cells of the invention into a non-human mammalian recipient at a location within said recipient able to support growth of said human fetal urinary bladder-derived epithelial cells, wherein said human fetal urinary bladder-derived epithelial cells have been recombined ex vivo with mesenchymal tissue able to effect differentiation of said human fetal urinary bladder-derived epithelial cells into human bladder epithelial cells.

In still another aspect, the invention relates to a population of human bladder epithelial cells differentiated from human fetal urinary bladder-derived epithelial cells generated by the process comprising administering the human fetal urinary bladder-derived epithelial cells of the invention into a non-human mammalian recipient at a location within said recipient able to support growth of said human fetal urinary bladder-derived epithelial cells, wherein said human fetal urinary bladder-derived epithelial cells have been recombined ex vivo with mesenchymal tissue able to effect differentiation of said human fetal urinary bladder-derived epithelial cells into human bladder epithelial cells.

In still another aspect, the invention relates to methods of generating a population of human prostate epithelial cells differentiated from human fetal urinary bladder-derived epithelial cells, comprising administering the human fetal urinary bladder-derived epithelial cells of the invention into a non-human mammalian recipient at a location within said recipient able to support growth of said human fetal urinary bladder-derived epithelial cells, wherein said human fetal urinary bladder-derived epithelial cells have been recombined ex vivo with mesenchymal tissue able to effect differentiation of said human fetal urinary bladder-derived epithelial cells into human prostate epithelial cells.

In still another aspect, the invention relates to a population of human prostate epithelial cells differentiated from human fetal urinary bladder-derived epithelial cells generated by the process comprising administering the human fetal urinary bladder-derived epithelial cells of the invention into a non-human mammalian recipient at a location within said recipient able to support growth of said human fetal urinary bladder-derived epithelial cells, wherein said human fetal urinary bladder-derived epithelial cells have been recombined ex vivo with mesenchymal tissue able to effect differentiation of said human fetal urinary bladder-derived epithelial cells into human prostate epithelial cells.

In still another aspect of this invention, the invention relates to methods of generating a human tissue model of human fetal prostatic epithelial cells using a substantially pure population of human fetal urinary bladder-derived epithelial cells and administering the human fetal urinary bladder-derived epithelial cells into a non-human, mammalian recipient.

In still another aspect of this invention, the invention relates to methods of generating a human bladder tissue model using a substantially pure population of human fetal urinary bladder-derived epithelial cells and administering the human fetal urinary bladder-derived epithelial cells into a non-human, mammalian recipient at a location within said recipient able to support growth of said human fetal urinary bladder-derived epithelial cells, wherein the human fetal urinary bladder-derived epithelial cells have been recombined ex vivo with mesenchymal tissue able to effect further differentiation of said human fatal urinary bladder-derived epithelial cells into human urinary bladder epithelial cells.

In still another aspect of this invention, the invention relates to a human bladder tissue model generated by the process comprising administering the human fetal urinary bladder-derived epithelial cells of the invention into a non-human mammalian recipient at a location within said recipient able to support growth of said human fetal urinary bladder-derived epithelial cells, wherein said human fetal urinary bladder-derived epithelial cells have been recombined ex vivo with mesenchymal tissue able to effect differentiation of said human fetal urinary bladder-derived epithelial cells into human bladder epithelial cells.

In still another aspect of this invention, the invention relates to methods of generating a human tissue model of human fetal prostatic epithelial cells using a substantially pure population of human fetal urinary bladder-derived epithelial cells and administering the human fetal urinary bladder-derived epithelial cells into a non-human, mammalian recipient.

In still another aspect of this invention, the invention relates to methods of generating a human prostate tissue model using a substantially pure population of human fetal urinary bladder-derived epithelial cells and administering the human fetal urinary bladder-derived epithelial cells into a non-human, mammalian recipient at a location within said recipient able to support growth of said human fetal urinary bladder-derived epithelial cells, wherein the human fetal urinary bladder-derived epithelial cells have been recombined ex vivo with mesenchymal tissue able to effect further differentiation of said human fatal urinary bladder-derived epithelial cells into human prostatic epithelial cells.

In still another aspect of this invention, the invention relates to a human prostate tissue model generated by the process comprising administering the human fetal urinary bladder-derived epithelial cells of the invention into a non-human mammalian recipient at a location within said recipient able to support growth of said human fetal urinary bladder-derived epithelial cells, wherein said human fetal urinary bladder-derived epithelial cells have been recombined ex vivo with mesenchymal tissue able to effect differentiation of the human fetal urinary bladder-derived epithelial cells into human prostate epithelial cells.

In another aspect of this invention, the invention relates to methods of providing cell therapy whereby a substantially pure population of human fetal urinary bladder-derived epithelial cells or cells differentiated therefrom are introduced into a recipient. In some embodiments, the invention relates to a method of providing cell therapy to a recipient, comprising administering to said recipient a plurality of human fetal urinary bladder-derived epithelial cells of the invention into said recipient wherein said human fetal urinary bladder-derived epithelial cells are first grown in serum-free media and then administered at a location within said recipient, said location being able to support growth and differentiation of said urinary bladder-derived epithelial cells. In some embodiments, the human fetal urinary bladder-derived epithelial cells of the invention are administered into the lumen of the recipients' urinary bladder.

In another aspect of this invention, the invention relates to methods of providing cell therapy whereby a substantially pure population of human prostatic epithelial cells differentiated from human fetal urinary bladder-derived epithelial cells are introduced into a recipient.

In another aspect of this invention, the invention relates to methods of providing a means for developing pharmaceutical drugs wherein a substantially pure population of human fetal urinary bladder-derived epithelial cells is used as a source of human urinary bladder epithelial cells or components of these cells as the targets of the drugs that are being developed.

In another aspect of this invention, the invention relates to methods of providing a means for developing pharmaceutical drugs wherein a substantially pure population of human fetal urinary bladder-derived epithelial cells is used as a source of human bladder epithelial cells or prostatic epithelial cells as the targets of the drugs that are being developed.

In another aspect of this invention, the invention relates to methods of providing a source of nucleic acids or proteins from those cells in a development of bioassays or for bioassays comprising isolating nucleic acids or proteins from the human fetal urinary bladder-derived epithelial cells and using said nucleic acids or proteins as one or more of the principal component in the bioassays. In another aspect, the invention relates to methods of providing a source of human fetal urinary bladder-derived epithelial cells in a development of bioassays or for bioassays comprising using human fetal urinary bladder-derived epithelial cells in the bioassays.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

FIG. 1B shows negative control without primary antibody. FIG. 1C shows staining with cytokeratin 7. FIG. 1D shows staining with anti-human smooth muscle alpha-actin. FIG. 1E shows staining with cytokeratin-19. FIG. 1F shows staining with uroplakin. The brown color areas are the positive staining and the blue color is the nuclear staining.

FIG. 2A is a photomicrograph of a section stained with hematoxylin and eosin (H&E). FIG. 2B shows a section that has been stained with an anti-human smooth muscle α-actin antibody. FIGS. 2C and 2D show staining with antibodies specific for human cytokeratins 7 and 19, respectively. Antibody binding is indicated by deposition of a brown reaction product. FIG. 2E shows a section which has been stained with anti-human uroplakin-III, and FIG. 2F shows a control (no primary antibody). Antibody binding, indicated by deposition of a dark purple/black reaction product, can be observed in FIG. 2E on the luminal surface.

FIG. 3A shows a photomicrograph of H&E staining of paraffin section of epithelial cell sheets released from the culture of bladder epithelial cell line before recombining with neonatal rat seminal vesicle mesenchyme. FIG. 3B shows a photomicrograph of H&E staining of paraffin sections of tissue recombinants of bladder epithelial cell line and rat seminal vesicle mesenchyme grown under SCID mouse kidney capsule for 6 months. Note the typical prostate structure. FIG. 3C shows a photomicrograph of immunohistochemical staining for prostate specific antigen (PSA) in the same tissue recombinants as in FIG. 3B. Note the strong positive brownish staining in the epithelial cell lining. The section was counter-stained by hematoxylin which stained the cellular nuclei in blue.

MODES FOR CARRYING OUT THE INVENTION

Figure 1:
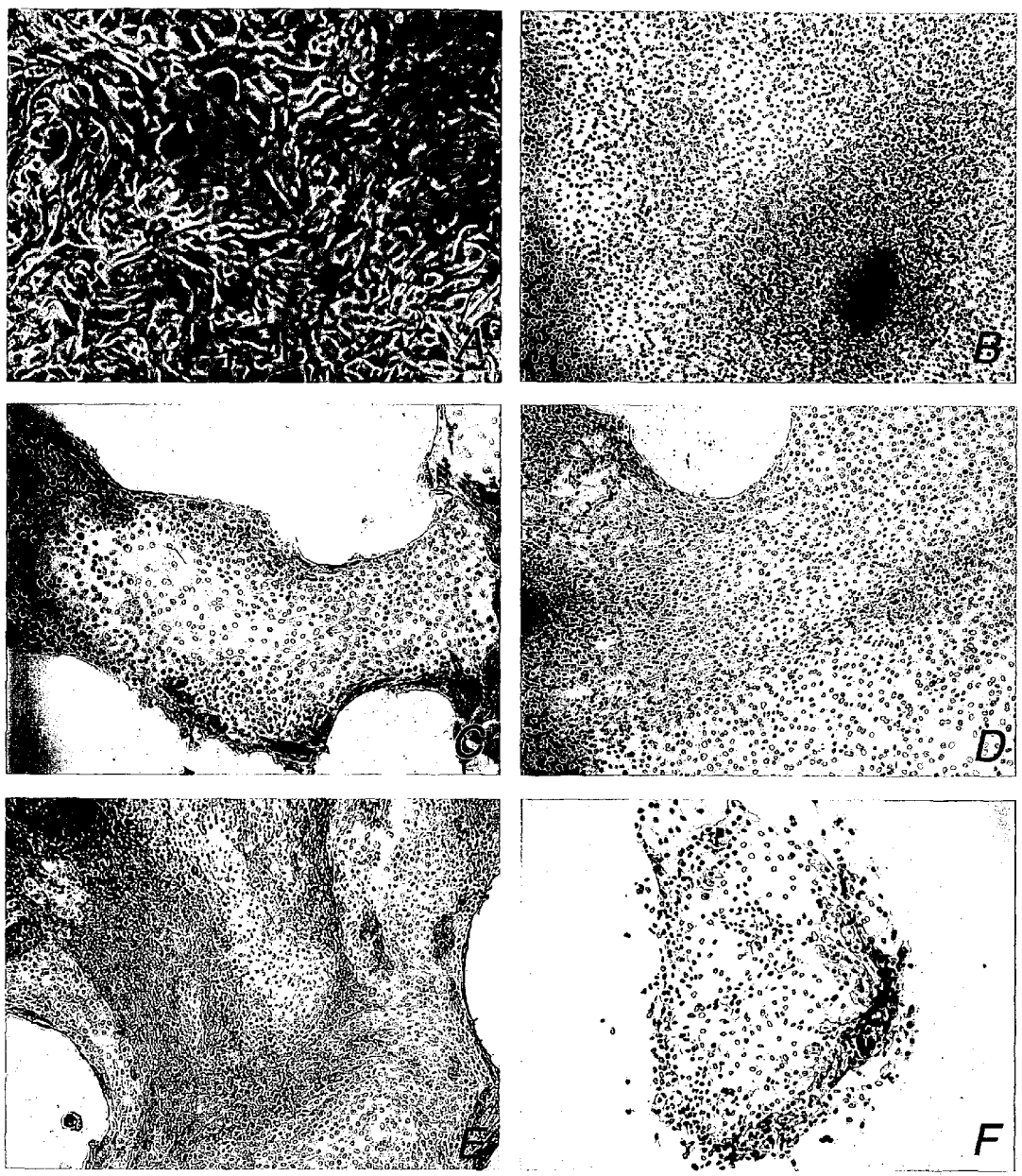
FIG. 1A shows a photomicrograph of a sample of passage 1 human fetal urinary bladder-derived epithelial cells observed under Phase contrast microscope 100× (Nikon).
FIGS. 1B, 1C, 1D, 1E, and 1F show photomicrographs of samples of immunohistochemistry (IHC) stained passage 1 human fetal urinary bladder-derived epithelial cells.

The following detailed description of the invention is provided to aid those skilled in the art in practicing the present invention. This detailed description should not be construed to limit the present invention, as modifications of the embodiments disclosed herein may be made by those of ordinary skill in the art without departing from the spirit and scope of the present invention. Throughout this disclosure, various publications, patents, and published patent specifications are referenced by citation. The disclosure of these publications, patents, and published patents are hereby incorporated by reference in their entirety into the present disclosure.

The practice of the present invention will employ, unless otherwise indicated, conventional techniques of immunology, molecular biology, microbiology, cell biology and recombinant DNA, which are within the skill of the art. See, e.g., *Molecular Cloning: a laboratory manual*, $2^{nd}$ edition Sambrook, et al. (1989); *Current Protocols In Molecular Biology* F. M. Ausubel, et al. eds., (1987); the series *Methods In Enzymology*, Academic Press, Inc.; *PCR 2: A Practical Approach*, M. J. MacPherson, B. D. Hames and G. R. Taylor, eds. (1995), *Antibodies, A Laboratory Manual*, Harlow and Lane, eds. (1988), *Adult and Pediatric Urology*, J. Gillenwater et al., eds. (2002), and *Animal Cell Culture*, R. I. Freshney, ed. (1987).

DEFINITIONS

As used in the specification and claims, the terms "urinary bladder-derived epithelial cells", "bladder-derived epithelial cells", and "bladder-derived cells" are used interchangeably and refer to cells derived from human fetal urinary bladder epithelial tissue. These cells are capable of dividing and of being passaged in vitro.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen binding site derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains.

The term "antigen" is a molecule which can include one or a plurality of epitopes to which an antibody can bind. An antigen is a substance which can have immunogenic properties, i.e., induce an immune response. Antigens are considered to be a type of immunogen. As used herein, the term "antigen" is intended to mean full length proteins as well as peptide fragments thereof containing or comprising one or a plurality of epitopes.

The terms "surface antigens" and "cell surface antigen" are used interchangeably herein and refer to the plasma membrane components of a cell. These component include, but are not limited to, integral and peripheral membrane proteins, glycoproteins, polysaccharides, lipids, and glycosylphosphatidylinositol (GPI)-linked proteins. An "integral membrane protein" is a transmembrane protein that extends across the lipid bilayer of the plasma membrane of a cell. A typical integral membrane protein consists of at least one membrane spanning segment that generally comprises hydrophobic amino acid residues. Peripheral membrane proteins do not extend into the hydrophobic interior of the lipid bilayer and they are bound to the membrane surface by noncovalent interaction with other membrane proteins. GPI-linked proteins are proteins which are held on the cell surface by a lipid tail which is inserted into the lipid bilayer.

"Immunogen" refers to any substance that induces an immune response. A substance that is an immunogen is described as being "immunogenic". Induction of immune response includes but is not limited to activation of humoral responses (e.g., producing antibodies) or cellular responses (e.g., priming cytotoxic T cells), inflammatory responses (e.g., recruitment of leukocytes), and secretion of cytokines and lymphokines.

The term "heterologous" as applied to a cell used for immunization or transplantation means that the cell is derived from a genotypically distinct entity from the recipient. For example, a heterologous cell may be derived from a different species or a different individual from the same species as the recipient. An embryonic cell derived from an individual of one species is heterologous to an adult of the same species. "Heterologous" as applied to a recipient means that the recipient is a genotypically distinct entity from the source of the cells that are being introduced into the recipient.

"Explant" refers to urinary bladder tissues taken out of a human fetus. Generally, explants are used as a source of urinary bladder-derived cells. Isolating the cells from the explant can be accomplished by several methods. One method is to place the urinary bladder epithelial tissue explant, either whole tissue or cut in smaller pieces, in a media and allow the epithelial cells to naturally migrate out of the solid tissue mass into the media. Another method is to subject the tissue to enzymatic digestion or to mechanical forces that forces cells away from the solid tissue.

A cell surface is "substantially free of serum biomolecules" when at least about 50% of the fetal urinary bladder-derived epithelial cell surfaces, more preferably at least about 75% of the fetal urinary bladder-derived epithelial cell surfaces, even more preferably at least about 90% of the fetal urinary bladder-derived epithelial cell surfaces, and most preferably at least about 95% of the fetal urinary bladder-derived epithelial cell surfaces do not have serum biomolecules derived from serum binding to the cell surface such that antigenic sites or antibody binding sites are bound or are unavailable for antigenic recognition by an antibody or a portion of an antibody. Cell surface can determined by measuring the cell size, either by microscopy or flow cytometry. For example, synthetic beads of various known sizes are commonly used for calibration in flow cytometry. A small quantity of calibrated bead may be mixed with bladder-derived epithelial cells and the resultant population is analyzed by flow cytometry. Bladder-derived epithelial cells can then be compared with the size of the calibrated beads. Calculations of cell surface amount can be accomplished since the sizes of the beads are known.

As used herein, a "substantially pure" population of cells is a population of cells that is comprised at least about 85% of the cells of interest, preferably at least about 90%, and even more preferably about 95% or more (such as 98% or more).

A "grafting recombinant", as used herein, refers to the combined unit of human fetal urinary bladder-derived cells and mesenchymal tissue. Mesenchymal tissue can be of urinary bladder-derived or non-urinary bladder-derived origin (e.g., bladder mesenchyme, seminal vesicle mesenchyme). Mesenchymal tissue can be from a species heterologous to the graft recipient. Mesenchymal tissue can also be from a non-human species. Grafting recombinants can be incubated on substrate, preferably a soft, biological substrate (e.g., agar) for a period ranging from 1 hour to 96 hours, more preferably between about 6 hours to 48 hours, and even more preferably, overnight with an incubation period of about 24 hours.

"Serum", as used herein, refers to the fluid phase of mammalian blood that remains after blood is allowed to clot.

"Serum biomolecules", as used herein, refers to biological compositions found in serum. Examples include, but are not limited to, albumin, $\alpha 1$-globulin, $\alpha 2$-globulin, $\beta$-globulin, and $\gamma$-globulin. Serum biomolecules can include biological compositions, whole or partial, that are either naturally found in serum or derived from processing and handling of serum.

The terms "mammals" or "mammalian" refer to warm blooded vertebrates which include but are not limited to humans, mice, rats, rabbits, simians, sport animals, and pets.

Isolation and Maintenance of Human Fetal Bladder-Derived Epithelial Cells

Fetal urinary bladder epithelial cells of this invention are isolated from human fetal urinary bladder tissue. The age of the fetus may be between about week 6 and about week 40, preferably between about week 8 and about week 30, more preferably between about week 14 and about week 21, more preferably about week 16 of gestation. The fetal urinary bladder can be identified by gross anatomy, outward appearance, and location within the fetus. The bladder is located at the midline in the inferior abdomen near the ventral wall. In addition to identification by location and appearance, the bladder can be identified by its attachment (via the bladder's superior surface) to the urachus (a remnant of the allantois that is known as the median umbilical ligament in the adult). Once identified, the fetal urinary bladder is excised and rinsed with phosphate buffered saline (PBS), preferably several times. Neighboring tissues and excess connective tissue is dissected away, and the bladder is again rinsed with PBS. The entire bladder is minced into cubes of approximately 1 mm, suspended in basal medium, transferred to a centrifuge tube, and centrifuged to pellet the minced tissue. The supernatant is removed, the tissue is resuspended in additional basal medium, then transferred to a culture dish. A wide variety of basal media can be used to keep the pH of the liquid in a range that promotes survival of fetal urinary bladder epithelial cells. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), OPTI-MEM® (GIBCO BRL) and Iscove's Modified Eagle's Medium (IMEM). In addition, any of the basal nutrient media described in Ham and McKeehan (1979) *Meth. Enz.,* 58:44, Barnes and Sato (1980) *Anal. Biochem.,* 102:255, or Mather, J. P. and Roberts, P. E. (1998) "Introduction to Cell and Tissue Culture", Plenum Press, New York can also be used.

Basal medium is added to the culture dish and the tissue is incubated at 37° C. in a humidified atmosphere. For more optimal conditions to promote fetal urinary bladder epithelial cell survival and growth, a variety of nutrients may be added to supplement the basal media (thus creating a "nutrient media"). Examples include, but are not limited to, insulin, transferrin, $\alpha$-tocopherol (vitamin E), progesterone, heregulin (HRG), keratinocyte growth factor (KGF), and aprotinin. In a preferred embodiment, the following amounts of nutrients are used to promote fetal urinary bladder epithelial cell survival and growth: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 0.1 µg/ml $\alpha$-tocopherol and not more than about 1 mg/ml $\alpha$-tocopherol, more preferably about 5 µg/ml $\alpha$-tocopherol; at least about 0.3 nM progesterone and not more than about 300 nM progesterone, more preferably about 3 nM progesterone; at least about 1 ng/ml KGF and not more than about 100 ng/ml KGF, more preferably about 10 ng/ml KGF, at least about 0.5 nM HRG and not more than about 500 nM HRG, more preferably about 5 nM HRG, and at least about 1 µg/ml aprotinin and not more than about 100 µg/ml aprotinin, more preferably about 25 µg/ml aprotinin. Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days). Human fetal urinary bladder epithelial cells are preferably cultured in serum-free medium.

Fetal urinary bladder epithelial cells migrate out of the fetal bladder tissue into the media in which the fetal bladder tissue is placed. In most instances, fibroblast-type cells also migrate out of the bladder tissue. The remnant of the minced tissues, which do not attach to the culture dish will flow in medium and will be cleaned up by medium change after a short time in culture, e.g., 1-2 weeks. Fibroblast-type cells are removed from the culture to generate a substantially pure population of fetal urinary bladder-derived epithelial cells. Preferably, fibroblast-type cells are removed by light proteolytic digestion of the culture, preferably in the presence of a calcium chelator such as EDTA. The cultures observed by microscopy, preferably utilizing an inverted phase contrast microscope, during the proteolytic treatment (e.g., with a trypsin-EDTA-solution, such as GIBCO BRL product no. 25300-054) to detect detachment of fibroblast-type cells. When the fibroblast-type cells are detached, they are removed from the culture by aspiration. The remaining cells in the culture are rinsed with PBS, and cultured in fresh medium.

The fetal urinary bladder epithelial cells can be grown in tissue culture containers (e.g., flasks, plates, etc.) that are either uncoated or coated with different substrates. Non-limiting examples of substrates that may be used include fibronectin, laminin, collagen, polylysine, nitrocellulose, nylon, and polytetrafluoroethylene. The size of the tissue culture containers is proportional to the amount of urinary bladder epithelial tissue being placed within the containers. A skilled artisan may determine the correct size of the tissue culture containers by a stepwise increment of fetal bladder tissue placed within the tissue culture containers. When the fetal bladder tissue is first placed within the tissue culture containers, the media is generally clear in overall turbidity. As cells migrate out and away from the bladder tissue pieces, the media will become more opaque and more turbid. At the point where the media is highly turbid, more nutrient media is placed in the tissue culture containers to replenish the nutrients consumed by the bladder-derived cells by adding more fresh medium or changing medium completely. Additionally or in the alternative, when the media becomes turbid, a small amount of cells may be removed from the tissue culture containers and checked for cell viability, for example, with trypan blue staining. Tissue culture containers that have been overrun with too many cells will begin to show decreased cell viability.

Continued culture of the fetal bladder-derived epithelial cells generally involves transfer of the cells to one or more new culture containers. Preferably, such transfer is done before the culture container is overrun with cells (e.g., as demonstrated by reduced cell viability. The cells may be transferred to other containers of a larger size (e.g., greater cubic volume) to accommodate the increasing amount of cells. Alternately, the cells may by 'split' into several separate tissue culture containers with fresh nutrient media (also known as "subculturing"). In this manner, a substantially pure population of fetal urinary bladder-derived epithelial cells can be obtained and propagated.

Removal of cells from a tissue culture container is preferably accomplished by enzymatic treatment to detach the cells from the surface(s) of the plastic tissue culture containers. In a more preferred embodiment, an enzyme such as collagenase-dispase is used in an effective amount to dissociate fetal urinary bladder epithelial cells from the sides of the tissue culture flask. An effective amount is at least about 10%, more preferably at least about 1%, and most preferably at least about 0.1% collagenase-dispase by weight. After detachment of cells from the surface(s) of the tissue culture container, the enzyme is washed away with a basal media, preferably the nutrient media disclosed herein, and the cells are placed in new culture containers with a nutrient media, preferably the nutrient media disclosed herein. In a preferred embodiment, keratinocyte growth factor (KGF), also called fibroblast growth factor 7 (FGF 7), and heregulin (HRG) are used as growth factors in the medium supplements for the urinary bladder-derived epithelial cell proliferation and longevity.

The frequency of feeding fetal urinary bladder-derived epithelial cells is dependent on the rate of nutrient metabolism of the cells. The higher rate of nutrient metabolism, the more frequent the cells need to be fed. Generally, media acidity will increase as cells metabolize nutrients in the media. Some nutrient media (e.g., RPMI-1640, DMEM, EMEM, etc.) contain pH-sensitive dyes that indicate the acidity such that media changes color when it becomes acidic. Nutrient media can then be added to bring acidity of the existing media to an acidity that will sustain life and promote growth of the cells. Alternatively, a small portion of the cells may be removed from the tissue culture container and assessed for cell viability, for example, with trypan blue staining. If the nutrient media has been metabolized, cell viability will be poor (e.g., less than 50%). A frequency of feeding that is preferable for promoting the survival and growth of fetal urinary bladder-derived epithelial cells is about twice a week. The fetal urinary bladder-derived epithelial cells of this invention can be passaged multiple (up to 12) times without senescence.

Characterization of Fetal Urinary Bladder-Derived Epithelial Cells

The population of fetal urinary bladder-derived epithelial cells of this invention isolated in the manner disclosed herein has several defining characteristics. Identification of fetal urinary bladder-derived epithelial cells may be accomplished by morphology or specific markers or a combination of both techniques.

The morphology of fetal urinary bladder-derived epithelial cells is characterized by transitional epithelial cell characteristics. The cells grow as clustered epithelial cell colonies. As transitional epithelium, the morphology varies somewhat. There are tight polygonal epithelial cells, elongated cells with slender processes and other cells of morphology in between. The elongated cells sometime formed bundles of cells. The tight polygonal cells appeared to be less differentiated bladder epithelial cells since these cells express less or no differentiated urothelial cell markers, such as cytokeratin 7 & 19, and uroplakin III. The elongated cells and cells of round enlarged morphology expressed more differentiated characteristics.

Markers that can be used to detect fetal urinary bladder-derived epithelial cells include but are not limited to cytokeratins (CK) 1, 5, 6, 7, 8, 10, 11, 13, 15, 16, 18, and 19 and uroplakins (e.g., uroplakins Ia, Ib, II, and III) on fetal urinary bladder-derived epithelial cell surfaces. These cell surface markers are assessed by employing antibodies specific for CK and uroplakins. Examples of antibodies that may be used include but are not limited to: anti-cytokeratin CK-7 (Zymed 18-0234 lot 00460118), CK-19 (NCL-CK 19 mouse monoclonal Novocastra Batch 100902) and anti-uroplakin antibodies (mouse anti-uroplakin III clone AUI, mIgGl Lot#105300a Cat #RD1-PR0651108, RDI). Anti-CK antibodies and anti-uroplakin antibodies can be used in either direct or indirect staining of bladder-derived epithelial cells in immunohistochemistry or by flow cytometry.

Fetal urinary bladder-derived epithelial cells have also been stained with anti-alpha-actin antibody (DAKOA/S Clone 1A4 Code M0851), which is smooth muscle actin marker. The result was negative, which indicates that the cultured fetal urinary bladder-derived epithelial cells do not contain any smooth muscle cells. Yet another marker which can be used for further characterization is H19 imprint gene, as exemplified in Example 3.

Uses of Fetal Urinary Bladder-Derived Epithelial Cells

Immunogen

A use for fetal urinary bladder-derived epithelial cells is as an immunogen. As disclosed in this invention, the unique serum-free culturing conditions allow the cell surfaces of the fetal urinary bladder-derived epithelial cells to remain free of serum proteins or serum biomolecules that may bind to the surface. A potential problem of antigenic sites that may be "masked" with binding by serum biomolecules is avoided by using the disclosed serum-free isolation and culturing techniques. Accordingly, a panel of antibodies may be generated to newly available antigens that were "masked" when using culture conditions containing serum.

Fetal urinary bladder-derived epithelial cells isolated and cultured with the methods disclosed herein can be used as an immunogen that is administered to a heterologous recipient. Methods of administrating fetal urinary bladder-derived cells as immunogens to a heterologous recipient include but are not limited to: immunization, administration to a membrane by direct contact such as swabbing or scratch apparatus, administration to mucous membrane by aerosol, and oral administration. As is well-known in the art, immunization can be either passive or active immunization. Methods of immunization can occur via different routes which include but are not limited to intraperitoneal injection, intradermal injection, local injection. The subjects of immunization may include mammals such as mice. The route and schedule of immunization are generally in keeping with established and conventional techniques for antibody stimulation and production. While mice are employed in this embodiment, any mammalian subject including humans or antibody producing cells therefrom can be manipulated according to the processes of this invention to serve as the basis for production of mammalian hybridoma cell lines. Typically, mice are inoculated intraperitoneally with an immunogenic amount of the fetal urinary bladder-derived cells and then boosted with similar amounts of the immunogen. In an alternative, cells grown on non-biological membrane matrix, are surgically implanted intraperitoneally into the host mammal. Lymphoid cells, preferably spleen lymphoid cells from the mice, are collected a few days after the final boost and a cell suspension is prepared therefrom for use in the fusion.

Hybridomas are prepared from the lymphocytes and immortalized myeloma cells using the general somatic cell hybridization technique of Kohler, B. and Milstein, C. (1975) Nature 256:495-497 as modified by Buck, D. W., et al., (1982) In Vitro, 18:377-381. Available myeloma lines, including but not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

In this manner, a panel of novel antibodies to cell surface antigen specific to fetal urinary bladder-derived epithelial cells can be generated using the fetal urinary bladder-derived epithelial cells of this invention. A population of monoclonal antibodies that bind to cell surface antigens representative of the human fetal urinary bladder-derived epithelial cells can also be generated using the method described in PCT WO 00/37503. Once monoclonal antibodies to cell surface antigens on fetal urinary bladder-derived epithelial cells are made by the method disclosed herein, the antibodies have several uses.

The antibodies may be sequenced and cloned for purposes of generating recombinant antibodies or humanized antibodies. Other uses of fetal urinary bladder-derived epithelial cell-specific antibodies include, but are not limited to, biological testing and purification (e.g., isolating fetal urinary bladder-derived epithelial cells by flow cytometry or panning), therapeutic uses (e.g., promoting or arresting cell growth by binding of antibody to target cell or promoting or arresting growth of a cell mass by binding of antibody to target cell), biological markers (e.g., identification of other fetal urinary bladder-derived cells), and clinical diagnosis (e.g., identification of cancerous urinary bladder epithelial cells).

Drug Discovery

Another use of human fetal urinary bladder-derived epithelial cells (or differentiated cells derived from human fetal urinary bladder-derived epithelial cells) is related to drug discovery. Since the human fetal urinary bladder-derived epithelial cell population has not been previously isolated and cultured in the disclosed manner, the fetal urinary bladder-derived epithelial cell population may secrete proteins that have not been heretofore discovered or characterized. Previous culturing techniques using serum may inhibit the secretion of proteins. Alternatively, proteins may change in function, conformation, or activity as they are being secreted and interacting with serum biomolecules. Proteins secreted by fetal urinary bladder-derived epithelial cells have minimal interference from serum biomolecules and thus, may be more physiologically and topologically accurate. Therefore, proteins secreted by fetal urinary bladder-derived epithelial cells may be used as targets for drug development. In one embodiment, drugs can be made to target specific proteins on fetal urinary bladder-derived epithelial cells and/or cells differentiated therefrom in vivo. Binding of the drug may promote differentiation of the urinary bladder cells into fully differentiated bladder epithelial cells. This approach may be useful when neogenesis of urinary bladder epithelial cells are desired, for example following radiotherapy involving the bladder or intravesicular chemotherapy (which can damage or destroy the bladder epithelium).

In yet another use, the human fetal urinary bladder-derived epithelial cells (or differentiated cells derived from human fetal urinary bladder-derived epithelial cells) can be used to develop or discover small molecules which interact with bladder-derived epithelial cells. These small molecules may be synthetic or natural and can be used to inhibit or promote growth and/or differentiation of the bladder-derived epithelial cells.

In yet another use, the human fetal urinary bladder-derived epithelial cells (or differentiated cells derived therefrom) can be used as a source of tissue specific components in a pharmaceutical development of one or more drugs and these components are used as targets for drugs under development.

Cell Therapy

In another use, fetal urinary bladder-derived epithelial cell lines are used for cell therapy. Transplantation of fetal urinary bladder-derived epithelial cells is one such example of cell therapy. To practice this use, fetal urinary bladder-derived epithelial cells are isolated and cultured in serum-free, nutrient-defined media using the methods disclosed. As disclosed herein, the cell population may be passaged to expand the number of available fetal urinary bladder-derived epithelial cells for transplantation. Fetal urinary bladder-derived epithelial cells can then be administered to a recipient and allowed to repopulate the lumenal surface of the urinary bladder. In an alternative, fetal urinary bladder-derived epithelial cells can be used as cellular carriers of gene therapy wherein fetal urinary bladder-derived epithelial cells are transfected with one or more genes and then administered to a recipient, preferably by intravesicular administration. In another embodiment, fetal urinary bladder-derived epithelial cells are used in a device (e.g., Theracyte®) which contains cells and limits access from other cells to limit immune system responses.

The plasticity of the fetal urinary bladder-derived epithelial cells of the invention may also be exploited in the prostatic context. Accordingly, fetal urinary bladder-derived epithelial cells may be transplanted into the prostate of an individual to repopulate or augment the prostatic epithelium. Fetal urinary bladder-derived epithelial cells may also be used as cellular carriers of gene therapy for delivery to the prostate, by administration of fetal urinary bladder-derived epithelial cells which have been genetically modified by, for example, transfection of one or more genes into the fetal urinary bladder-derived epithelial cells, followed by transplantation into the prostate.

Human Tissue Models

Another use for fetal urinary bladder-derived epithelial cells is to create human tissue models in non-human mammals. Fetal urinary bladder-derived epithelial cells are placed on top of mesenchymal tissue to form grafting recombinants. The mesenchymal tissue may be either urinary bladder-derived or non-urinary bladder-derived tissue and may be derived from a different species from which fetal urinary bladder-derived epithelial cells are isolated. In a working example, human fetal urinary bladder-derived epithelial cells are placed on top of rat bladder mesenchymal tissue to form a graft recombinant. Another exemplary grafting recombinant is fetal urinary bladder-derived epithelial cells placed on top of prostatic mesenchyme (e.g., rat seminal vesicle mesenchyme). A skilled artisan may determine the optimal combination in a stepwise fashion, by first isolating human fetal urinary bladder-derived epithelial cells using the methods disclosed herein and then combining with mesenchymal tissue from different organs. In some embodiments, a different species, e.g., rat, is used as a source for mesenchymal tissue in combination with human fetal urinary bladder-derived epithelial cells. The use of heterologous species allows human-specific markers to be used to determine the identity of differentiated fetal urinary bladder-derived cells. The likelihood of false positives is reduced if rat mesenchymal tissue is used.

A graft recombinant comprising fetal urinary bladder-derived epithelial cell spheres placed on mesenchymal tissue is cultured on a soft substrate, such as agar, preferably about half a day to about 3 days, more preferably about one day, and then placed under the kidney capsule of a recipient mammal. Possible recipient mammals include but are not limited to mice and rats. Typically in graft situations, donor tissue is vulnerable to attack by the recipient's immune system. To alleviate graft rejection, several techniques may be used. One method is to irradiate the recipient with a sub-lethal dose of radiation to destroy immune cells that may attack the graft. Another method is to give the recipient cyclosporin or other T cell immunosuppressive drugs. With the use of mice as recipient mammals, a wider variety of methods are possible for alleviating graft rejection. One such method is the use of an immunodeficient mouse (nude or severe combined immunodeficiency or SCID).

In working examples, human fetal urinary bladder-derived epithelial cell spheres are placed on rat bladder mesenchymal tissue or rat seminal vesicle mesenchyme and placed under the kidney capsule of an immunodeficient mouse. The graft recombinant remains in the recipient for about 1 week to about 52 weeks, preferably about 5 weeks to about 40 weeks, more preferably about 6 weeks to about 10 weeks, and even more preferably about 8 weeks before the grafts are harvested and analyzed for fetal urinary bladder-derived epithelial cell differentiation. In some cases, a small portion of the graft is needed for analysis. Markers specific for the fetal urinary bladder-derived epithelial cells and cells derived therefrom as disclosed herein may be utilized in an immunohistochemical analysis. In addition, a combination of one or more of these markers may be used in combination with cell morphology to determine the efficacy of the transplantation.

In one embodiment, human fetal urinary bladder-derived model is generated in a SCID (severe combined immunodeficiency) mouse. This fetal urinary bladder-derived model can be made by utilizing the human fetal urinary bladder-derived epithelial cells isolated and cultured with methods disclosed herein and using the human fetal urinary bladder-derived epithelial cells to make graft recombinants. Graft recombinants are then placed under the kidney capsule of mice. After about 1 to 10 weeks, preferably about 6 to 8 weeks after implantation under the kidney capsule, the graft or portion thereof is harvested and analyzed by immunohistochemistry. Cell surface markers on fetal urinary bladder-derived epithelial cells that may be used include, but are not limited to, CK 1, 5, 6, 7, 8, 10, 11, 13, 15, 16, 18, and 19, prostate specific antigen (PSA), acidic alkaline phosphatase, uroplakins Ia, Ib, II, and III, and H19 imprinted gene. The anti-CK antibodies or anti-uroplakin antibodies disclosed herein are used to analyze the efficacy of the bladder tissue model system, while PSA antibodies are useful in analyzing the prostate tissue model system. Yet another way to assess the results of fetal urinary bladder-derived epithelial cell differentiation is by morphology. Urinary bladder-derived epithelial cells form a transitional epithelium, and when recombined with bladder mesenchymal tissue will always form a hollow structure lined with bladder epithelium. Urinary bladder-derived epithelial cells recombined with seminal vesicle mesenchyme adopt a morphology typical of prostate epithelium. Morphology can be combined with cell surface markers for a more complete assessment.

Invention also provides, through these methods, ways to produce populations of differentiated human bladder epithelial cells and human prostate epithelial cells.

Bioassays

The human fetal urinary bladder-derived epithelial cells (or cells differentiated therefrom) and components of these cells disclosed herein can be used in various bioassays. In one use, the bladder-derived epithelial cells are used to determine which biological factors are required for differentiation. By using the bladder-derived epithelial cells in a stepwise fashion in combination with different biological compounds (such as hormones, specific growth factors, etc.), one or more specific biological compounds can be found to induce differentiation to bladder cells or to prostate cells.

The invention also provides methods of providing a source of nucleic acids or proteins for bioassays comprising isolating nucleic acids or proteins from the human fetal urinary bladder-derived epithelial cells and using said nucleic acids or proteins as one or more of the principal component in the bioassays. Other uses in a bioassay for bladder-derived epithelial cells are differential display (e.g., mRNA differential display) and protein-protein interactions using secreted proteins from bladder-derived epithelial cells. Protein-protein interactions can be determined with techniques such as yeast two-hybrid system. Proteins from bladder-derived epithelial cells can be used to identify other unknown proteins or other cell types that interact with bladder-derived epithelial cells. These unknown proteins may be one or more of the following: growth factors, hormones, enzymes, transcription factors, translational factors, and tumor suppressors. Bioassays involving bladder-derived epithelial cells and the protein-protein interaction these cells form and the effects of protein-protein or even cell-cell contact may be used to determine how surrounding tissue, such as mesenchymal tissue, contributes to bladder-derived epithelial cell differentiation.

The following examples provide a detailed description of the isolation, characterization, and use of fetal urinary bladder-derived epithelial cells. These examples are not intended to limit the invention in any way.

EXAMPLES

Example 1

Isolation of Fetal Urinary Bladder-Derived Epithelial Cells

Human fetal bladder tissue, gestational age from 14-21 weeks, was obtained from Advanced Bioscience Research at Alameda, Calif. As soon as the tissues arrived, they were rinsed three times with 20 ml of cool PBS. The bladders were cleaned of excess connective tissue, rinsed an additional two times with cool PBS, then cut into small segments (approximately 1 mm mince) with a razor blade or a pair of scissors under dissecting a microscope.

The minced tissue was suspended in 10 ml of OPTI-MEM® (Invitrogen Life Technologies), then transferred into a 15 ml centrifuge tube using a plastic pipette which had been pre-coated with bovine serum albumin to minimize tissue binding to the walls of the pipet. The minced tissue was centrifuged at 1000 rpm for 5 minutes in Heraeus Megafuge 2.0 (Cat#75003485) to pellet the minced tissue. The supernatant was aspirated and the pellet resuspended in 6 ml of fresh OPTI-MEM®.

The tissue suspension was transferred and divided into the 6 wells of a tissue culture treated six-well tissue culture plate. An additional 3 ml of nutrient medium (10 µg/ml insulin, 10 µg/ml transferrin, 5 µg/ml α-tocopherol (Sigma catalog no. T3251), 25 µg/ml aprotinin, 3 nM progesterone, 10 ng/ml KGF, 5 nM HRG, 100 µg/ml gentamycin in OPTI-MEM®) was added to the well, then the plate was incubated at 37° C. in a humidified incubator with a 95% air, 5% $CO_2$ atmosphere. Gentamycin was not used after the first two days of culture.

Fibroblasts were removed from the culture by limited proteolysis. The cultures were briefly trypsinized with 0.5 ml of 0.05% EDTA-trypsin (Gibco BRL) and observed under a phase contrast microscope until the fibroblast cells shrank. The plate was shaken thoroughly and the fibroblast cells came off the plate. When the fibroblast cells became detached from the substrate, they were removed by aspirating the medium and detached cells. The cultures were rinsed with 5 ml of PBS twice, then fed with fresh nutrient medium.

The resulting purified populations of fetal urinary bladder-derived epithelial cells were passaged up to twelve times. The cells were detached from the culture vessel by trypsinization (1 ml of 0.05% trypsin-EDTA, Invitrogen Life Technologies catalog no. 25300-054) or collagenase/dispase (3 mg/ml), Roche Molecular Biochemicals (Cat No. 269 638)). The detached cells were collected, pelleted (1000 rpm for 5 minutes), washed twice with basic medium, resuspended in fresh nutrient medium, and replated.

Example 2

Immunohistochemical Characterization

Monolayers of fetal urinary bladder-derived epithelial cells cultured in four-well chamber slides were washed three times with cool PBS and fixed with 100% reagent alcohol at −20° C. for 5 minutes. Then, the fixed slides were air dried overnight. The cells were incubated sequentially in blocking buffer (5% goat serum in PBS) for about 1 hour, in primary antibodies for overnight, and in peroxidase-conjugated affinipure $F(ab)_2$ fragment of goat anti-mouse IgG+IgM(H+L) for about 1 hour. The cells were washed three times with PBS for 5 minutes per wash between those steps. The primary antibodies used were cytokeratins 7 and 19, uroplakin III, and alpha-actin at the dilution recommended by the supplier. To visualize staining of cells by the antibodies, the fetal urinary bladder-derived epithelial cells were incubated in peroxidase substrate $DAB/H_2O_2$ prepared from Sigma.

Some cells were positive for uroplakin III and cytokeratins 7 and 19. Those cells were usually located toward the edges of epithelial colonies. Less differentiated cells located in the center of epithelial colonies were negative for those markers. None of the cells in culture were positive for α-actin. Positive staining with uroplakin III, a highly specific marker for urinary bladder epithelium, indicates that the cells are urinary bladder epithelium, while the lack of staining with α-actin indicates that the cultures are not contaminated with smooth muscle cells.

Example 3

Detection of Fetal Bladder Cell Molecular Marker H19 Imprinted Gene mRNA

H19 imprinted gene mRNA has been characterized as a marker specifically expressed in fetal human bladder cells but not expressed in normal human adult bladder cells (Elkin et al., 1995, *FEBS Lett.* 374(1):57-61; Cooper et al., 1996, *J. Urol.* 155(6):2120-27). To detect H19 mRNA, replicate fetal bladder-derived epithelial cell cultures of passage 2, approximately $10^5$ cells each, were extracted for total RNA with RNeasy kit (Cat#74104) purchased from Qiagen according to the protocol provided by the supplier. The final total RNA was eluted in 50 µl water for each sample. The total RNA, 9.5 µl for each sample, was reverse transcribed into first strand cDNA in a 20 µl reaction with a cDNA synthesizing kit (Promega Corporation Cat A3500) with random primer according to the protocol provided by the supplier. PCR reactions were set up as following with high fidelity PCR master mix manufactured by Roche Biochemical (Cat #2 140 314).

TABLE 1

| Reagent | No RT control | RT-PCR |
| --- | --- | --- |
| Template | 1 µl total RNA | 2 µl/cDNA |
| H19F* | µl | µl |
| H19R** | µl | µl |
| Water | 22 µl | 21 µl |
| High fidelity PCR master mix | 25 µl | 25 µl |

*Sequence of H19F primer: 5'-ttccaggcagaaagagcaag-3'
**Sequence of H19R primer: 5'-tgccatgtccctgtctgac-3'

Both primers were synthesized by Invitrogen custom oligonucleotide synthesis and dissolved in water at a concentration of 2.5 O.D. 260 nm/ml. The predicted PCR product for specific H19 mRNA using this pair of primers was 117 base pairs.

The PCR reaction was carried out in a Techne Genius™ thermocycler set at 3 minutes at 94° C. for initial denaturing, 25 cycles of 30 seconds at 94° C. for denaturing and 30 seconds at 60° C. for annealing and extension. Final extension was at 72° C. for 7 minutes. The PCR products were fractionated by electrophoresis in 2% agarose gel prepared in Tris Borate Buffer at 80 volt for 2 hours, stained with ethidium bromide, and visualized by illumination with UV light. Fluorescence photographs were taken with a Kodak image station 440 CF.

Amplification of human fetal bladder-derived epithelial cell CDNA resulted in a clear band of PCR amplification product of the predicted size (approximately 17 bp). No amplification product was observed when total RNA was used as template. This result confirmed the RT-PCR products were amplified from H19 mRNA.

Example 4

Human Bladder Tissue Modeling

Bladder mesenchyme were dissected from newborn (24 hour) Sprague-Dawley rat pups and transferred to a dish containing 1% Trypsin and incubated at 4° C. for 90 minutes. The medium was the removed and then rudiments washed several times in DMEM containing 20% FBS to neutralize trypsin activity. Bladder epithelium and associated mesenchyme were then further separated under a dissecting microscope. To make the tissue recombinants, the mesenchyme, free of associated epithelium, was placed on the surface of a 0.4% agar plate containing DMEM with 1% FBS. It should be noted that these brief exposures of the mesenchyme and tissue recombinants to serum-containing medium are not considered "culturing" in serum-containing medium.

Primary fetal human bladder-derived epithelial cells were harvested by treatment with 0.5% collagenase/dispase. The bladder-derived epithelial cells came off as sheets. The cell sheets were then placed on top of the mesenchyme by a sterile forceps and the tissues were incubated overnight at 37° C. in a humidified atmosphere of 95% air: 5% $CO_2$. The next day tissue recombinants were transplanted under the renal capsule of CD1 nude mice.

The host mouse was sacrificed 8 weeks after grafting, the tissues recovered and fixed in 10% neutral formalin overnight. The fixed tissues were dehydrated by the use of a series of graded ethanol solutions, and cleared in Histo-Clear solution. Tissues were then embedded in paraffin and cut at 6 µm. For basic staining, the sections were de-waxed in Histo-Clear, re-hydrated in graded ethanol solutions and stained with hematoxylin and eosin (H&E).

For immunohistochemistry, anti-human smooth muscle alpha-actin, anti-human uroplakin, anti-human cytokeratin 7, and anti-human cytokeratin 19 antibodies were used. For cytokeratin 7 and 19 immunohistochemistry, an antigen retrieval protocol was performed. Briefly, the sections were soaked in Target Retrieval solution (Dako, Cat #1699, 1:10 dilution from 10× stock), heated with microwave (Panasonic, Model NN-7523, 120 V, 12.8 A) on high power for 30 minutes, and then allowed to cool down to the room temperature (about 25° C.). Antigen retrieval was not performed for anti-human smooth muscle α-actin and uroplakin III.

The sections were blocked with 3% $H_2O_2$ in Milli-Q $H_2O$ for 20 minutes and rinsed three times with 1×PBS for 2 minutes per wash. The sections were then circled with an Immedge™ pen (Vector Laboratories, catalog no. H-4000) and washed once with 0.5% Tween-20 in 1×PBS for 2 minutes. The sections were further blocked with 5% goat serum in 1×PBS (blocking buffer) for 1 hour. The primary antibodies were then added to cover the section (about 500 µl). Primary antibodies used were mouse anti-human smooth muscle α-actin (Dako Cat. #M0851, used undiluted), mouse anti-uroplakin III clone AU1 (Cat #RDI-PR0651108, Research Diagnostic Inc., Flanders, N.J., at 1:500 dilution), mouse anti-human cytokeratin 7 (Cat #18-0234, Zymed, at 1:50), and mouse anti-human cytokeratin 19 NCL-CK19 (Cat #100902, Novocastra, at 1:100). Primary antibody incubation took place at 4° C. overnight.

Following overnight incubation, excess primary antibodies were drained and the sections were rinsed three times with 1×PBS containing 0.5% Tween-20 for 2 minutes per wash. The secondary antibody, 1:500 diluted of biotinylated goat-anti-mouse immunoglobulin antibody (Cat #E0433, Dako), was added (500 µl for each section) and incubated at room temperature for 1 hour. The sections were rinsed again three times with 1×PBS containing 0.5% Tween-20 for 2 minutes per wash and processed further with Vectastain ABC Elite kit (Cat #PK-6100, Vector) according to protocol provided by the manufacturer. The slides were developed in 1 mg/ml DAB solution (diaminobenzidine, Sigma, Cat #D-5905) in 0.1 M NaAc, pH 5.0 containing 0.015% hydrogen peroxide. Finally the slides were washed in water, counter-stained with hematoxylin (Cat #HXHHEGAL, American Master Tech Scientific) to identify nuclei, and dehydrated in graded ethanol (70%, 80%, 95%, 100%) (Harleco, Cat #65347/85).

Figure 2:
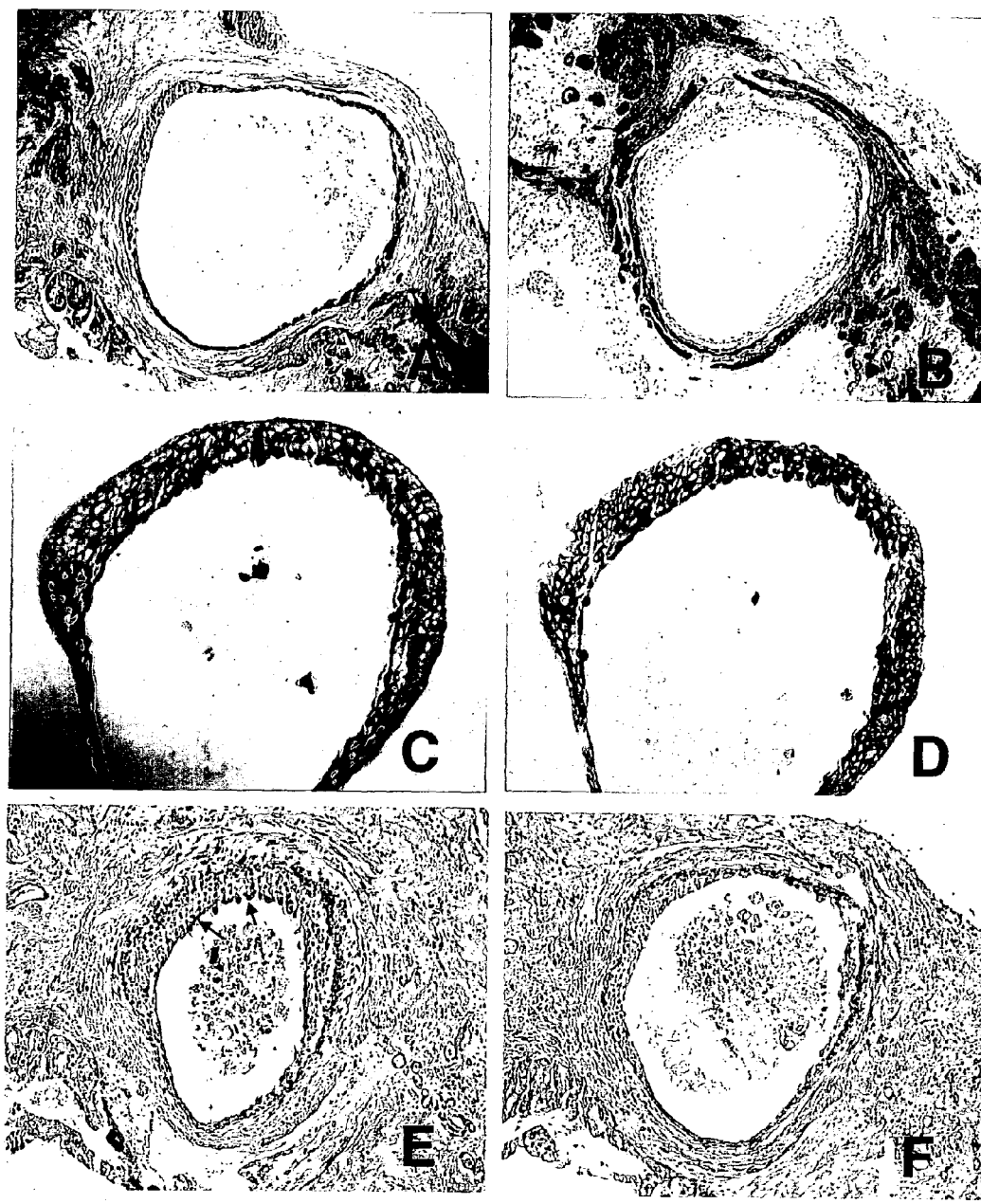
FIG. 2 shows photomicrographs of sections from a tissue recombinant comprising human fetal urinary bladder-derived epithelial cells and rat bladder mesenchyme.

Results are shown in FIGS. 1 and 2. FIG. 1a shows an H&E stained section of tissue recombinant. FIGS. 1b, 1c, and 1d show α-actin, human cytokeratin 7, and human cytokeratin 19 staining, respectively. Note that the cytokeratin staining is limited to the epithelial layer lining the lumen formed within the tissue recombinant. FIG. 2a shows staining with an anti-human uroplakin antibody (FIG. 2b is a secondary antibody-only control). Staining is limited to the lumenal surface of the epithelial layer in the recombinant, as is found in normal, in situ urinary bladder epithelium. It should be noted that anti-uroplakin III antibodies stain only part of the fetal urinary bladder-derived epithelium, indicating variable levels of differentiation of the fetal urinary bladder-derived epithelial cells within the tissue recombinant.

Example 5

Human Prostate Tissue Modeling

Seminal vesicle mesenchyme was dissected from newborn (day of birth) Sprague-Dawley rat pups and transferred to a dish containing 1% Trypsin and incubated at 4° C. for 90 minutes. The medium was the removed and then rudiments washed several times in DMEM containing 20% FBS to neutralize trypsin activity. Seminal vesicle epithelium and associated mesenchyme were then further separated under a dissecting microscope. To make the tissue recombinants, the mesenchyme, free of associated epithelium, was placed on the surface of a 0.4% agar plate containing DMEM with FBS, and human fetal bladder-epithelium derived cells, cultured and harvested as described in Example 4, were placed on the mesenchyme and allowed to adhere overnight at 37° C. in a humidified atmosphere of 95% air: 5% $CO_2$. It should be noted that these brief exposures of the mesenchyme and tissue recombinants to serum-containing medium are not considered "culturing" in serum-containing medium.

The tissue recombinants were transplanted under the kidney capsules of male SCID mice. The hosts were sacrificed six months after transplantation and the grafts were recovered.

Figure 3:
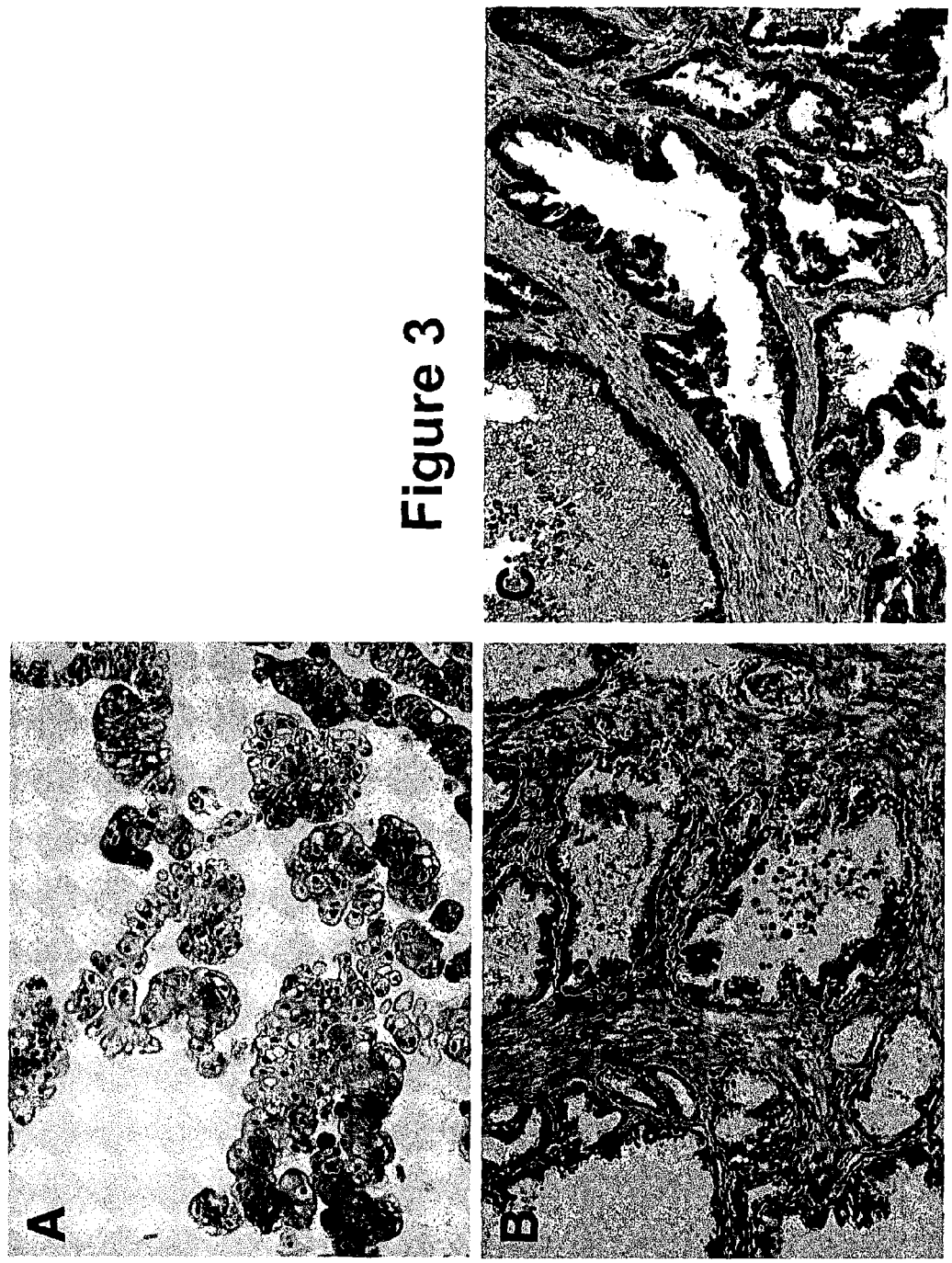
FIG. 3. Differentiation of human bladder epithelial cell line into prostatic epithelial cells in tissue recombinant.

The fixed tissues were processed as in Example 4 and stained for prostate specific antigen by immunohistochemistry. For immunohistochemistry, sections were deparaffinized with histoclear and hydrated through serial baths of ethanol into phosphate-buffered saline. Endogenous peroxidase was blocked by 3% hydrogen peroxide for 15 minutes. The tissue sections were then incubated with antibody against prostate specific antigen (Dako corporation, California) for overnight at 4° C. Samples were washed in PBS then incubated in secondary antibody (goat anti-mouse biotinylated, dako corporation, California), followed by incubation in avidin-biotin complex. Staining was developed in diamino benzidine (DAB). Samples were washed extensively in water to remove excessive DAB, dehydrated in graded alcohol, cleared in Xylene and mounted with coverslips. The result showed the bladder epithelial cells when recombined with seminal vesicle mesenchyme have differentiated morphologically and biochemically into prostatic epithelial cells, as showed in the FIG. 3.

What is claimed is:

1. A method of isolating a substantially pure population of human fetal urinary bladder epithelial cells having a capacity to differentiate into either differentiated bladder or prostate epithelium, wherein said cells are positive for molecular marker H19 imprinted gene mRNA and lacking alpha-actin expression, comprising:
   (a) microdissecting human fetal urinary bladder tissue at gestational age from 14-21 weeks;
   (b) placing the microdissected human fetal urinary bladder tissue in a serum-free nutrient medium under culture conditions sufficient to sustain fetal urinary bladder epithelial cells wherein the serum-free medium contains nutrients comprising insulin, transferrin, α-tocopherol, and aprotinin;
   (c) maintaining suitable culture conditions sufficient to allow the migration of fetal urinary bladder epithelial cells from the human fetal urinary bladder tissue into the serum-free nutrient medium; and
   (d) maintaining suitable culture conditions to obtain a substantially pure population of fetal urinary bladder epithelial cells having a capacity to differentiate into differentiated bladder or prostate epithelium.

2. The method of claim 1, wherein said serum-free nutrient medium further comprises progesterone, keratinocyte growth factor (KGF) and heregulin (HRG).

3. A substantially pure isolated population of human fetal urinary bladder epithelial cells having a capacity to differentiate into either differentiated bladder or prostate epithelium, wherein said cells are positive for molecular marker H19 imprinted gene mRNA and lacking alpha-actin expression, produced by the process comprising:
   (a) microdissecting human fetal urinary bladder tissue at gestational age from 14-21 weeks;
   (b) placing the microdissected human fetal urinary bladder tissue in a serum-free nutrient medium under culture conditions sufficient to sustain fetal urinary bladder epithelial cells wherein the serum-free medium contains nutrients comprising insulin, transferrin, α-tocopherol, and aprotinin;
   (c) maintaining suitable culture conditions sufficient to allow the migration of fetal urinary bladder epithelial cells from the human fetal urinary bladder tissue into the serum-free nutrient medium; and
   (d) maintaining suitable culture conditions to obtain a substantially pure population of urinary bladder epithelial cells.

4. The population of cells of claim 3, wherein the serum-free nutrient medium used in said process further comprises progesterone, keratinocyte growth factor (KGF) and heregulin (HRG).

5. A substantially pure isolated population of human fetal urinary bladder epithelial cells established from human fetal bladder tissue at gestational age from 14-21 weeks wherein said cells have a capacity to differentiate into either differentiated bladder or prostate epithelium and wherein said cells are positive for molecular marker H19 imprinted gene mRNA and lacking alpha-actin expression.

* * * * *

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
ttccaggcag aaagagcaag                                             20

<210> SEQ ID NO 2
<211> LENGTH: 19
<212> TYPE: DNA
<213> ORGANISM: Artificial Sequence
<220> FEATURE:
<223> OTHER INFORMATION: PCR Primer

<400> SEQUENCE: 2
tgccatgtcc ctgtctgac                                              19
```